United States Patent
Van Mechelen et al.

(10) Patent No.: US 9,423,791 B2
(45) Date of Patent: Aug. 23, 2016

(54) SENSOR SYSTEM AND METHOD FOR DETERMINING PAPER SHEET QUALITY PARAMETERS

(71) Applicant: ABB RESEARCH LTD, Zürich (CH)

(72) Inventors: Jacobus Lodevicus Martinus Van Mechelen, Regensdorf (CH); Hannes Merbold, Zürich (CH)

(73) Assignee: ABB Research Ltd, Zurich (CH)

( * ) Notice: Subject to any disclaimer, the term of this patent is extended or adjusted under 35 U.S.C. 154(b) by 340 days.

(21) Appl. No.: 14/218,603

(22) Filed: Mar. 1, 2014

(65) Prior Publication Data
US 2014/0277674 A1    Sep. 18, 2014

(30) Foreign Application Priority Data
Mar. 18, 2013    (EP) ..................... 13159746

(51) Int. Cl.
*G06F 19/00*    (2011.01)
*G06F 7/66*    (2006.01)
(Continued)

(52) U.S. Cl.
CPC .......... *G05B 19/41875* (2013.01); *G01B 11/06* (2013.01); *G01B 11/0625* (2013.01); *G01N 21/3559* (2013.01); *G01N 21/3581* (2013.01); *G01N 21/86* (2013.01); *G01N 33/346* (2013.01)

(58) Field of Classification Search
CPC ............. G05F 1/66; H02J 7/345; H02J 3/381; H02J 3/32; Y10T 307/516; D21G 9/0054
USPC .......................... 700/109, 117, 122, 127, 129
See application file for complete search history.

(56) References Cited

U.S. PATENT DOCUMENTS

| | | | |
|---|---|---|---|
| 6,479,822 B1 * | 11/2002 | Nelson | G01N 21/3581 250/338.1 |
| 7,609,366 B2 * | 10/2009 | MacHattie | D21G 9/0036 162/198 |

(Continued)

FOREIGN PATENT DOCUMENTS

| | | | | |
|---|---|---|---|---|
| CA | 2 549 576 A1 | 12/2006 | | |
| WO | WO2009/062315 | * 5/2009 | ............. | G01N 21/17 |

(Continued)

OTHER PUBLICATIONS

European Search Report for EP 13159746.0 dated Jun. 3, 2013.

*Primary Examiner* — Ronald Hartman, Jr.
(74) *Attorney, Agent, or Firm* — Taft Stettinius & Hollister LLP (57) ABSTRACT

A non-contact sensor system and method are disclosed for determining paper sheet quality parameters such as caliper, basis weight and sheet moisture based on THz radiation. The method can include emitting, by an emitter system, a THz radiation signal towards paper sheet material such that the THz radiation interacts with the paper sheet material; detecting, by a detector system, a time and/or frequency dependent response of the THz radiation signal having interacted with the paper sheet material; determining model parameters of a physical model by optimizing the model parameters such that a predicted response of the physical model is fitted to the detected response, the model parameters being indicative of transmission and/or reflection coefficients at interfaces of the paper sheet material with surrounding media; and determining, from the determined model parameters, at least some of the paper sheet quality parameters.

20 Claims, 4 Drawing Sheets

(51) Int. Cl.
  *G05B 19/418* (2006.01)
  *G01N 21/86* (2006.01)
  *G01B 11/06* (2006.01)
  *G01N 33/34* (2006.01)
  *G01N 21/3581* (2014.01)
  *G01N 21/3559* (2014.01)

(56) References Cited

U.S. PATENT DOCUMENTS

| | | | | |
|---|---|---|---|---|
| 7,829,855 B2 * | 11/2010 | Reid | ...... | G01N 21/23 250/341.3 |
| 7,837,833 B2 * | 11/2010 | Jez | ...... | G01N 21/23 162/198 |
| 7,968,860 B2 * | 6/2011 | Haran | ...... | G01N 21/55 250/339.1 |
| 8,144,370 B2 * | 3/2012 | Itsuji | ...... | G01N 21/3581 324/640 |
| 8,187,424 B2 * | 5/2012 | Haran | ...... | D21F 7/003 162/198 |
| 9,140,542 B2 * | 9/2015 | Savard | ...... | G01B 11/0625 |
| 2009/0027655 A1 * | 1/2009 | Haran | ...... | G01N 21/55 356/51 |
| 2009/0101297 A1 | 4/2009 | Jez et al. | | |
| 2009/0128799 A1 | 5/2009 | MacHattie et al. | | |
| 2010/0024999 A1 * | 2/2010 | Haran | ...... | D21F 7/003 162/198 |
| 2011/0026026 A1 | 2/2011 | Jez et al. | | |
| 2013/0220158 A1 * | 8/2013 | Vassilev | ...... | G01N 21/3559 101/484 |

FOREIGN PATENT DOCUMENTS

| WO | WO2012/057699 | * | 5/2012 | ............ B41F 33/00 |
|---|---|---|---|---|
| WO | WO2013/116924 | * | 8/2013 | ............ G01B 11/06 |

* cited by examiner

SENSOR SYSTEM AND METHOD FOR DETERMINING PAPER SHEET QUALITY PARAMETERS

RELATED APPLICATION

This application claims priority under 35 U.S.C. §119 to European Patent Application No. 13159746.0 filed in Europe on Mar. 18, 2014, the entire content of which is hereby incorporated by reference in its entirety.

FIELD

The present disclosure relates to a method for determining paper sheet quality parameters such as sheet caliper, basis weight, moisture and the like by a non-contact sensor system using THz radiation. Further aspects relate to a corresponding sensor system and to an apparatus for handling paper sheet material having such a sensor system.

BACKGROUND INFORMATION

Quality control of sheet materials like paper can be crucial for industrial processes such as paper processing (e.g. in paper production), for reasons that range from economical optimization to physical performance. There are two types of quality control: off-line and in-line. Off-line quality control takes place outside of the paper processing, e.g. as post processing verification, and is often carried out in a laboratory. In contrast, in-line quality control takes place in real time as part of the paper processing. In-line quality control can, for example, be performed at the dry end of the process and may serve as feedback for the wet end process. Parameters determined for in-line quality control of paper can include caliper (thickness), basis weight, moisture, ash, brightness, gloss and color of the paper. Other parameters like coat weight and fiber orientation and anisotropy may be determined as well.

Current in-line quality control systems typically consist of heavy weight frames on which a sensor head box is mounted containing many sensor elements, each of which is used to characterize an individual parameter of the running paper sheet. The sensor head scans perpendicular to the paper feed direction to obtain a representative measure of the quality of the processed material. Some of the sensors of a typical sensor head may require beta radiation which needs particular shielding and care. Some other sensors require physical contact with the paper sheet material and may therefore interfere with the paper handling, e.g. by increasing the risk of damaging the paper.

Recently, a contactless measurement technique using THz radiation has been proposed. A system for in-line measurements of sheet caliper based on THz radiation has been described in US 2009/0128799 A1.

Nevertheless, there is still a need for a system that extracts the relevant quality parameters from a THz measurement signal in a reliable manner for obtaining robust and meaningful quality parameters.

SUMMARY

A method is disclosed of determining a plurality of paper sheet quality parameters of a paper sheet material based on fitting to a physical model by a non-contact sensor system, wherein the paper sheet quality parameters include at least sheet caliper, basis weight, and sheet moisture, and wherein the sensor system includes an emitter system for emitting THz radiation, a detector system for detecting THz radiation, and a processing unit operationally coupled to the emitter system and the detector system, the method comprising: emitting, by the emitter system, a THz radiation signal towards the paper sheet material such that the THz radiation interacts with the paper sheet material; detecting, by the detector system, a time and/or frequency dependent response of the THz radiation signal having interacted with the paper sheet material; determining model parameters of the physical model by optimizing the model parameters such that a simulated response of the physical model is fitted to the detected response, the model parameters being indicative of transmission and/or reflection coefficients at interfaces of the paper sheet material with surrounding media; and determining, from the determined model parameters, at least one of the paper sheet quality parameters, hereby the model parameters of the physical model are fitted to the detected response by an iterative procedure comprising: (a) calculating a simulated response based on the physical model using an initial guess for the model parameters; (b) calculating an error function expressing a deviation between the simulated response and the detected response; (c) iterating steps (a) and (b), whereby the model parameters are varied until the error function satisfies a best-fit criterion; and (d) obtaining fitted model parameters as final parameters satisfying the best-fit criterion in step (c), and calculating at least one of the paper sheet quality parameters from the fitted model parameters.

A sensor system is also disclosed for determining a plurality of paper sheet quality parameters of a paper sheet material in a non-contact manner, the sensor system comprising: an emitter system for emitting THz radiation; a detector system for detecting THz radiation; and a processing unit operationally coupled to the emitter system and the detector system, and configured for determining the plurality of paper sheet quality parameters by: emitting, by the emitter system, a THz radiation signal towards the paper sheet material such that the THz radiation interacts with the paper sheet material; detecting, by the detector system, a time and/or frequency dependent response of the THz radiation signal having interacted with the paper sheet material; determining model parameters of the physical model by optimizing the model parameters such that a simulated response of the physical model is fitted to the detected response, the model parameters being indicative of transmission and/or reflection coefficients at interfaces of the paper sheet material with surrounding media; and determining, from the determined model parameters, at least one of the paper sheet quality parameters, whereby the model parameters of the physical model will be fitted to the detected response by an iterative procedure comprising: (a) calculating a simulated response based on the physical model using an initial guess for the model parameters; (b) calculating an error function expressing a deviation between the simulated response and the detected response; (c) iterating steps (a) and (b), whereby the model parameters are varied until the error function satisfies a best-fit criterion; and (d) obtaining fitted model parameters as final parameters satisfying the best-fit criterion in step (c), and calculating at least one of the paper sheet quality parameters from the fitted model parameters.

BRIEF DESCRIPTION OF THE FIGURES

The details will be described in the following with reference to the figures, wherein.

DETAILED DESCRIPTION

According to a first aspect, a method for determining a plurality of paper sheet quality parameters of a paper sheet material by a non-contact sensor system is provided. The paper sheet quality parameters comprise at least sheet caliper, basis weight, and preferably also sheet moisture. The sensor system comprises an emitter system for emitting THz radiation, a detector system for detecting THz radiation, and a processing unit operationally coupled to the emitter system and the detector system. The method is based on fitting to a physical model and comprises: emitting, by the emitter system, a THz radiation signal towards the paper sheet material such that the THz radiation interacts with the paper sheet material; detecting, by the detector system, a time and/or frequency dependent response of the THz radiation signal having interacted with the paper sheet material; determining model parameters of a physical model by optimizing the model parameters such that a predicted response of the physical model is fitted to the detected response, the model parameters being indicative of transmission and/or reflection coefficients at interfaces of the paper sheet material with surrounding media; and determining, from the determined model parameters, at least one of the paper sheet quality parameters (e.g., caliper and preferably also basis weight).

According to a second aspect, a sensor system for determining a plurality of paper sheet quality parameters of a paper sheet material in a non-contact manner is provided. The sensor system comprises: an emitter system for emitting THz radiation, a detector system for detecting THz radiation, and a processing unit operationally coupled to the emitter system and the detector system. The sensor system is configured for determining the plurality of paper sheet quality parameters by the (any) method as described herein.

The sensor assembly and method allow for obtaining a robust and meaningful set of quality parameters using a large amount of information from the detected THz radiation response of the sheet material by fitting the predicted response of a physical model to the detected response.

Further advantages, features, aspects and details that can be combined with embodiments described herein are evident from the description and the drawings.

In the following, some more detailed aspects of exemplary embodiments of the invention are described. Aspects and parts of aspects are independent of each other and can be combined in any manner. For example, any aspect or embodiment described in this document can be combined with any other aspect or embodiment.

First, some general aspects and definitions are described. According to an aspect of the invention, a method and system for determination of a plurality of sheet quality parameters by non-contact measurement using THz radiation is obtained.

According to a further aspect, a plurality of the sheet quality parameters is obtained coincidentally, using a measurement from the same data source(s). The data source(s) include a THz sensor system. Preferably, a single measured waveform or spectrum is used for determining the quality parameters. Preferably, no material specific calibration data is used for obtaining the quality parameters.

The paper sheet quality parameters to be determined include at least sheet caliper (i.e. thickness), basis weight, and preferably sheet moisture. Optionally other paper sheet quality parameters are included as well, such as coat weight, fiber orientation, fiber anisotropy, and ash (i.e. content of non-burnable elements). According to the method, all these parameters are to be determined by a non-contact sensor system, i.e. a system that obtains these parameters without physically contacting the paper sheet material. In particular, the sensor system is an optical system that determines all paper sheet quality parameters by detecting and analysing electromagnetic THz radiation that has interacted with the paper sheet material. Herein, THz radiation is defined as electromagnetic radiation of (i.e. including a non-negligible signal component having) a frequency in the range of 0.01-10 THz. The detected signal (e.g. time-domain waveform or frequency-domain spectrum of the detected THz radiation) is also referred to as the response of the (emitted) THz radiation signal.

The THz radiation signal is analysed by optimizing parameters of a physical model such as to obtain a best-fit of the model prediction to the detected radiation. This ensures a reliable analysis that takes into account the entire information contained in the detected THz radiation signal. Therefore, the result is robust even in the presence of noise, because is based on a large number of data points, even if only one or a few time-traces are measured. Further, this approach allows the result to be consistent with a realistic understanding of the underlying physical phenomena present in the paper sheet material. The physical model may be an effective model for optically relevant parameters of the paper.

Once the model parameters are determined, at least some of the paper sheet quality parameters are then calculated from the model parameters.

Herein, a physical model is defined as a function of the predicted response in terms of model parameters, based on physical considerations. The model parameters are indicative of (allow calculating) the transmission and/or reflection coefficients at interfaces of the paper sheet material with surrounding media.

The choice of these model parameters is advantageous because the transmission and/or reflection coefficients, or a suitable parametrization thereof, allow for calculating at least some of the paper sheet quality parameters relatively straightforwardly. At the same time, the transmission and/or reflection coefficients are directly linked to the detected response of the THz signal having interacted with the paper sheet material, and thereby allows for a good and robust model of the response of the THz signal having interacted with the paper sheet material that does not necessitate any calibration parameters. Therefore, these transmission and/or reflection coefficients (or parameters indicative of them) are advantageously used as the model parameters.

Examples of possible model parameters indicative of the transmission and/or reflection coefficients include the (complex) index of refraction of the paper sheet material, or a parametrization thereof. Other possible model parameters include the transmission and/or reflection coefficients themselves.

Preferably, the physical model is chosen such that it allows for a parametrization of the transmission and/or reflection coefficients having dependence on frequency, and/or possibly allowing for individual transmission and/or reflection coefficients for each optical axis of the paper sheet material (birefringence). In an example, a frequency dependence can be obtained by expressing the transmission and/or reflection coefficients in terms of a frequency-dependent index of refraction. A frequency-dependent index of refraction, n(f), in turn, may be parametrized in various manners. For example, the functional form of n(f) may be expressed by a number of parameters based on physical considerations, or using a parametrization that approximates the expected frequency dependence sufficiently well. One example is the following parametrization:

$$n(f)=n_0+\Sigma_k n_k * p_k(f) \quad (1)$$

Herein, n(f) the frequency-dependent index of refraction, f is frequency, k=1 ... N is an index (N being a natural number, e.g. N=1), and $n_0$, $n_k$, are the model parameters, and $p_k(f)$ is a frequency dependent function that represents physical phenomena in paper.

The parametrization of equations (1) has not only the advantage of approximating the expected form of the paper's index of refraction well, but also allows for a physical interpretation of the frequency-dependency being caused by oscillating modes in the paper sheet material.

The transmission and/or reflection coefficients can then be expressed in terms of the (frequency-dependent) index of refraction n(f) via Fresnel equations, for example. Other parametrizations of the transmission and/or reflection coefficients are possible as well. Thus, according to a general aspect, the model parameters may be parameters expressing the index of transmission and/or the index of reflection and/or the refractive index.

Next, some aspects relating to the algorithm for finding the optimized (best-fit) predicted response are described in more detail. The algorithm includes the following input data: a reference waveform (in time domain) or reference spectrum (in frequency domain) or some other signal sequence describing the emitted THz radiation signal not having interacted with the paper sheet material, and the detected response. In addition, an ambient moisture value and/or a temperature value may be inputted.

Preferably, an iterative algorithm is used. The iterative algorithm includes the following steps: (a) calculating a simulated response based on the physical model using an initial guess for the model parameters; (b) calculating an error function expressing a deviation between the predicted response and the detected response; (c) iterating steps (a) and (b), whereby the model parameters are varied until the error function satisfies a best-fit criterion, and (d) obtaining the fitted parameters as the final parameters satisfying the best-fit criterion in step (c). Then, at least some of the quality parameters (e.g. caliper, basis weight and/or coating weight) are calculated from the fitted parameters.

The sheet quality parameters are thus determined by calculating a best-fit response as a function of the model parameters, such that the best-fit response satisfies a predetermined best-fit criterion for an error function expressing a deviation between the predicted response and the detected response.

The best-fit criterion may include a minimization criterion for the error function (e.g. $L^2$ norm). Possibly, additional terms may be added to the error function, e.g. "penalty terms" that penalize a physically implausible predicted response.

Next, some aspects relating to the analyzed THz radiation signal are described in more detail. According to a general aspect, the model parameters are determined using the entire detected response (essentially all data points of the detected response). Thus, essentially all data points of the response are input and used in the calculation of the model parameters, in the sense that a variation in any one of the data points influences the result at least in a minimal manner (not taking into account rounding or truncating of numbers). For example, if the response is a time-domain waveform with a given sample rate the entire shape (essentially all data points) of the time-domain waveform is used.

According to a further aspect, a detected response covers a time of at least 500 fs. Hence, all data points which are used cover at least 500 fs signal length. Preferably, the response covers even at least 1 ps or at least 2 ps. According to a further aspect, a detected response has a time resolution (average spacing of data points in time, also referred to as the reciprocal value of the sampling rate) of at least 100 fs. Hence, at least one data point per 100 fs time interval is used. Preferably, the sampling rate is at least 0.02 $fs^{-1}$. According to a further aspect, the THz radiation is a pulsed beam, and preferably the entire pulse is used for determining the model parameters.

According to a further aspect, all of the paper sheet quality parameters (i.e. at least sheet caliper, basis weight and any other claimed paper sheet quality parameters) are determined from a single THz radiation signal (possibly having two polarization components) as the response. The radiation signal may be a continuous signal, a THz pulse or part of a THz pulse.

According to a further aspect, the duration of the measurement (i.e. the length of time it takes to obtain the above-mentioned time trace) is less than the average homogeneity length of the paper sheet material divided by the maximum rated propagation speed of the paper sheet material relative to the sensor assembly in the apparatus for handling the paper sheet material. In the absence of any information to the contrary, the homogeneity length is the average fiber length, typically 2.5 mm to 4 mm.

According to a further aspect, the determining of the quality parameters includes a combination of several different analysis methods using a single common THz radiation signal (response) as an input. The analysis methods may include the parameter fitting described above, and additionally at least one of a spectral analysis of the detected response or of a quantity derived therefrom. Since all parameters are obtained from a single detected response, obtained by a measurement at a single location within the fiber length homogeneity on the sheet material, mutual use of intermediate parameters of the analysis does not introduce errors.

According to a general aspect, some of the quality parameters are obtained by analyzing a time-domain waveform of the response, and some of the quality parameters are obtained by analyzing a frequency-domain spectrum of the same response. For example, caliper and basis weight and optionally coating weight are obtained from the time-domain waveform; moisture and optionally ash may be obtained from the frequency-domain spectrum.

Next, some aspects relating to further input data are described in more detail. According to an aspect, the determining of the paper sheet quality parameters takes place without input of any calibration data specific for the kind of paper sheet material. Herein, this calibration data is understood as external input data, not coming from the THz detector, for which the kind of paper sheet material needs to be specified. Thus, for example, the radiation detected by the detector system, as well as possibly temperature and ambient moisture, are not calibration data, because no input of the kind of paper sheet material is necessary. Further, pre-stored parameters such as fundamental optical transition probabilities of specific substances like water or ash and material constants are not calibration data as long as they are independent of the kind of paper sheet material used. In contrast, calibration data necessitates an input of the kind of paper sheet material, typically by manual input (e.g. through keyboard or through a barcode reader). The advantage of using a physical model is that a reliable result can be obtained without input of such calibration data.

According to a further aspect, the sensor system further comprises an air moisture sensor and/or a temperature sensor operationally coupled to the processing unit, wherein the method further comprises obtaining an ambient air moisture value from the air moisture sensor obtaining a temperature value from the temperature sensor, and inputting the obtained temperature value and/or the ambient air moisture value in the processing unit.

Next, some aspects relating to the geometrical arrangement of the sensor apparatus are described in more detail. According to an aspect, the sensor system comprises a back-side THz reflector. Further, the emitter system and the detector system may be arranged on one side of the paper sheet material and the back-side THz reflector may be arranged on the other side of the paper sheet material. The THz reflector may include a layer of metal, glass, silicon, or of another material having an index of refraction in the relevant frequency range that is strongly different from that of the ambient medium. The THz reflector may be arranged substantially in parallel to the paper sheet material.

According to a further aspect, the sensor system may comprise a semitransparent THz reflector as beam splitter. The beam splitter may be arranged at an angle with respect to the paper sheet, such that an optical path from the emitter system and an optical path to the detector system are guided to/from a common optical path that is substantially perpendicular to the paper sheet material. As a result, the emitter system and the detector system are arranged for respectively emitting and detecting light rays having a right angle of incidence with respect to the paper sheet material.

Next, some aspects relating to the determining of specific quality parameters are described in more detail. Herein, first some aspects of the fiber orientation determining are described: The detector system is sensitive to polarized THz radiation of mutually different polarization states (i.e. can distinguish between such polarization states, such as two or more different linear, circular or elliptical polarization states). Preferably at least two of the different polarization states are inclined at an angle other than 90° with respect to each other. The fiber orientation determining may include at least one of the following: In the emitting step, the THz radiation signal emitted by the emitter system has more than one linearly polarized component (e.g. at least one circular or elliptical polarization or two independent linear polarizations).

According to a further aspect, the THz radiation detector system is sensitive to at least two independent linear polarization directions, preferably to three independent linear polarization directions, i.e. is capable of resolving a signal difference between these polarization directions. Accordingly, in the detecting step, the detected time and/or frequency dependent response is detected for each of the at least two polarization directions (preferably simultaneously). In the step of determining model parameters, a respective set of detection-frame model parameters are determined for each of the two polarization directions, the detection-frame model parameters being indicative of the transmission and/or reflection coefficients at the interfaces of the paper sheet material with the surrounding media in the respective polarization direction.

According to a further aspect, the method further comprises determining, from the detection-frame model parameters, the fiber orientation as an optical axis (one of the optical axes) of the paper sheet material. According to a further aspect, the method further comprises combining the detection-frame model parameters dependent on the angle between the respective (linear) polarization directions and the determined optical axis, thereby obtaining axis-frame model parameters indicative of the transmission and/or reflection coefficients at the interfaces of the paper sheet material with the surrounding media for a direction parallel to the determined optical axis and for a direction perpendicular to the determined optical axis, respectively. This combination can, for example, be obtained by a linear transformation of the detection-frame model parameters, in particular by rotating them by a rotation angle which is the difference between one of the polarization directions and the optical axis. For example, the model parameters may include Jones parameters in a detection-frame, and the rotation is achieved by 2×2 rotation matrices depending on the rotation angle. According to a further aspect, at least one of the remaining paper sheet quality parameters, other than fiber orientation, and possibly anisotropy, are then determined from the rotated (axis-frame) parameters.

According to a further aspect, the determined optical axis, or a direction perpendicular to the determined optical axis, is output as the fiber orientation. According to a further aspect, the optical parameters are parametrized in terms of Jones parameters, e.g. of a complex 2×2-matrix describing the interaction with the electromagnetic field.

According to a further aspect, the optical anisotropy is determined dependent on frequency. According to this aspect, the frequency-dependent response spectrum is obtained e.g. by Fourier transformation of the time-domain response waveform. The steps for determining the optical anisotropy are then performed for each frequency individually. Thereby, a frequency-dependent optical anisotropy is obtained.

Next, some aspects of the ash and/or moisture determining are described. According to an aspect, the ash/moisture is determined e.g. from the spectral weight of a contribution to the index of refraction (e.g. from a parameter $n_k$ in eq. (1)) or other determined model parameter representing the ash content. According to another aspect, the ash/moisture is determined from a frequency-dependent optical coefficient (e.g. transmission, reflection or absorption coefficient or index of refraction), e.g. by spectral analysis of that coefficient.

Next, some aspects relating to possible sensor systems and apparatuses are described in more detail. According to an aspect, the sensor system comprises an emitter system for emitting THz radiation, a detector system for detecting THz radiation, and a processing unit operationally coupled to the emitter system and the detector system, and is configured for (i.e. equipped and programmed for) determining the plurality of paper sheet quality parameters by the method according to any aspect described herein. For this purpose, a memory of the processing unit may be equipped with program code for causing a processor of the processing unit to execute the method according to any aspect described herein.

According to a further aspect, the apparatus further comprises a paper sheet transport system for transporting the paper sheet material, and the sensor system is arranged for determining a plurality of paper sheet quality parameters in-line, i.e. while the paper sheet material is being transported and preferably processed by the paper sheet transport system. According to a further aspect, the determined parameters are used for adjusting the operation of at least one paper processing section dependent on the paper sheet quality parameters. In this manner, a feedback control loop is created.

According to a further aspect, the emitter system and the detector system are moved transversally with respect to a feeding direction of the paper sheet material. Thereby, the paper can be analysed at different transversal positions. Correspondingly, the apparatus may comprise a sensor mount that is transversally movable with respect to a feeding direction of the paper sheet material, wherein the emitter system and the detector system are mounted on the sensor mount.

Reference will now be made in detail to the various embodiments, one or more examples of which are illustrated in each figure. Each example is provided by way of explanation and is not meant as a limitation. For example, features illustrated or described as part of one embodiment can be used on or in conjunction with any other embodiment to yield yet a further embodiment. It is intended that the present disclosure includes such modifications and variations.

Within the following description of the drawings, the same reference numbers refer to the same or to similar components. Generally, only the differences with respect to the individual embodiments are described. Unless specified otherwise, the description of a part or aspect in one embodiment applies to a corresponding part or aspect in another embodiment as well.

Figure 1:
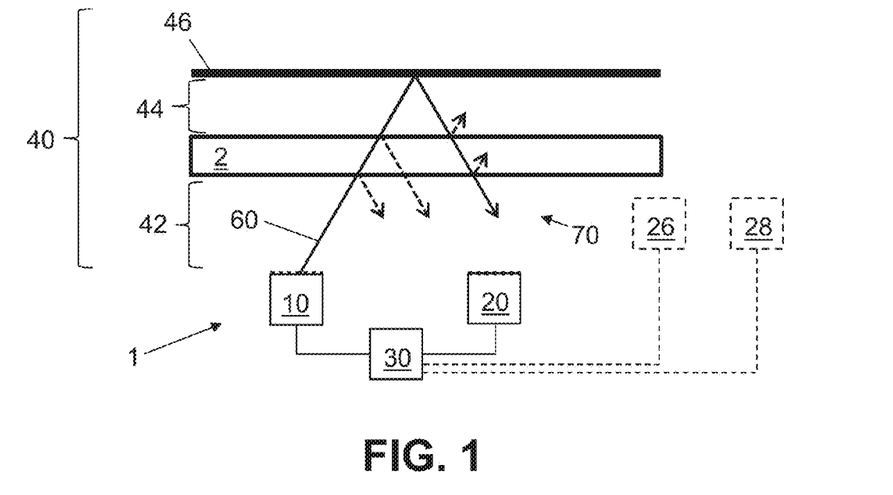
FIG. 1 is a schematic side view of a sensor system according to an exemplary embodiment.

FIG. 1 is a schematic side view of a sensor system 1 according to an embodiment of the invention. The sensor system 1 has an emitter system 10 for emitting THz radiation, a detector system 20 for detecting THz radiation, a processing unit 30 operationally coupled to the emitter system 10 and the detector system 20, and a THz reflector 46. In addition, FIG. 1 shows an optional air moisture sensor 26 and an optional temperature sensor 28 which are operationally coupled to the processing unit 30.

Further, a paper sheet material 2 is arranged between the emitter system 10 (and the detector system 20) on the one hand and the THz reflector 46 on the other hand, with an air gap 42 between the emitter, detector systems 10, 20 and the paper sheet material 2, and with an air gap 44 between the paper sheet material 2 and the THz reflector 46. The THz reflector 46 thus acts as a back-side reflector, with the emitter system 10 and the detector system 20 being arranged on one side of the paper sheet material 2 and the reflector 46 being arranged on the other side of the paper sheet material 2.

FIG. 1 also shows the path of a THz radiation signal 60 emitted from the emitter system 10. The THz radiation signal 60 (solid line) traverses the air gap 42, the paper sheet material 2 and the air gap 44, is reflected by the reflector 46, again traverses the air gaps and the paper sheet material 2 in reverse order, and is finally detected by the detector system 20. During this propagation, portions of the THz radiation signal 60 interact with the paper sheet material 2, e.g. are reflected at an interface of the paper sheet material 2 with the surrounding media (air gaps 42, 44), as indicated by dashed lines, and/or are absorbed, decelerated and undergo a phase shift, or otherwise interact with the paper sheet material 2 while being transmitted there through. The result of all these interactions is a THz radiation response 70 having interacted with the paper sheet material 2, which is detected by the detector system 20.

The interaction of the electromagnetic radiation with this multilayer stack (air gaps 42, 44, paper sheet material 2, reflector 46) creates a complex pattern of reflected and transmitted signals that are detected, by the detector system 20, as a function of time (waveform in time domain) and/or as a function of frequency (spectrum in frequency domain) or in some other manner. The following explanation is mainly based on time-domain. However, analogous considerations also apply to the frequency-domain response, which is a Fourier transform of time-domain response and therefore contains a similar (same) amount of information. Hence, while the discussion herein is mainly based on the time-domain waveform, it may also be adapted to frequency-domain analysis of the spectrum (or some other representation of the waveform). The processing section 30 receives the response waveform (THz radiation response) 70, and also receives (or has stored therein) the waveform emitted by the emitter. The processing section 30 then performs an analysis of the response waveform (taking into account the original waveform and other information such as detected moisture and/or temperature), and thereby obtains the quality parameters by the method described herein.

Figure 2A:
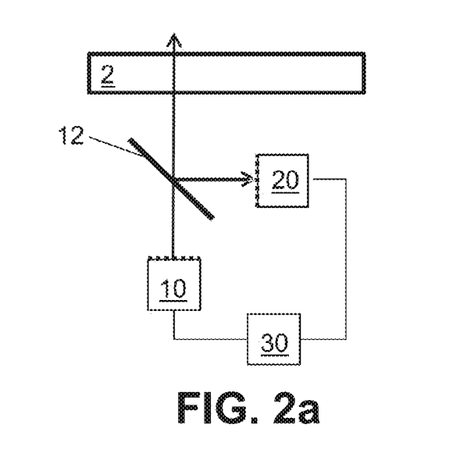
FIGS. 2a and 2b are schematic side views of possible further details and variants of the sensor system of FIG. 1.
Figure 2B:
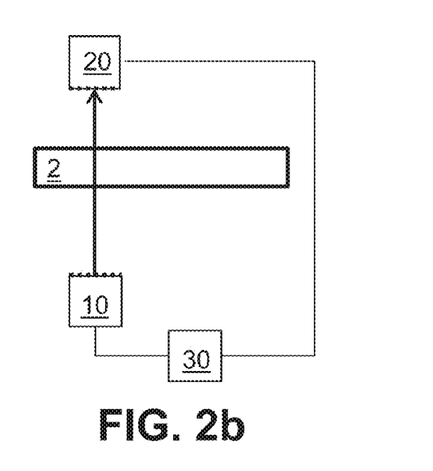

In FIG. 1, as well as in FIGS. 3a-3c discussed further below, the radiation is shown to propagate along an angle with respect to the normal direction of the paper sheet material 2. This direction of propagation is mainly for illustration purposes, because it allows for visually separating the incoming and reflected THz radiation. In the actual setup, the main direction of propagation of the THz radiation is preferably orthogonal to the paper sheet material, as shown in FIGS. 2a and 2b below, so that the transmitted and received THz signals are collinear and normal to the surface of the paper sheet material 2. In this manner, a maximum portion of the reflected signals in captured by the detector, and the reflection is minimally influenced by the geometry and maximally reflects the properties of the material 2, because the Fresnel equations expressing the transmission/reflection take a particularly simple form.

FIGS. 2a and 2b are schematic side views of possible further details of possible implementations or variants of the sensor system of FIG. 1. In FIG. 2, the emitter system 10 and the detector system 20 are arranged with their axes at an angle (here: 90°), and a beam splitter 12 is arranged such as to co-align the axes, so that the transmitted and received THz signals are collinear and normal to the surface of the paper sheet material 2.

In FIG. 2b, the emitter system 10 and the detector system 20 are arranged on opposite sides of the paper sheet material 2 with their optical axis (direct line between them) being substantially orthogonal to the paper sheet material 2. In this manner, a simple transmission measurement is performed instead of the double-transmission measurement (due to reflector 46) of the embodiment of FIG. 1.

In the following and with reference to further Figures, specific aspects for obtaining individual quality parameters are described in more detail. First, some aspects for obtaining caliper are described.

Figure 3A:
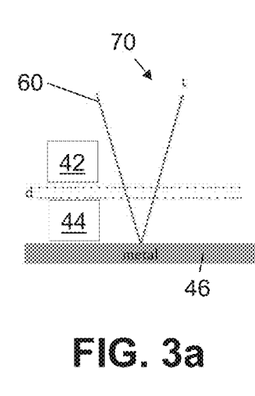
FIGS. 3a to 3c are schematic views illustrating the interaction with paper sheet material of THz radiation emitted by a sensor system according to an exemplary embodiment.
Figure 3B:
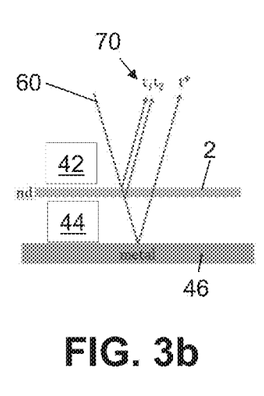
Figure 3C:
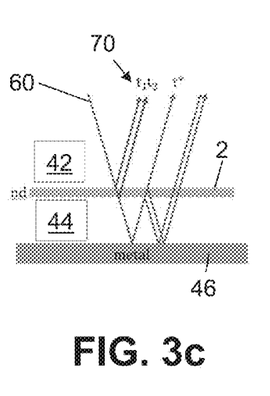

FIGS. 3a to 3c are schematic views illustrating the interaction with paper sheet material of THz radiation emitted by a sensor system according to an embodiment of the invention. Herein, FIG. 3a shows the setup of FIG. 1 without the sheet material 2 of FIG. 1; FIGS. 3b and 3c show the setup with the sheet material 2. The description of FIG. 1 analogously applies to FIGS. 3a to 3c. Also, FIGS. 3a-3c show the emitted THz radiation signal 60 and the THz radiation response 70 to be detected as rays (lines) analogously to FIG. 1.

In the following, it is briefly made plausible that the resulting waveform of the THz radiation response 70 contains sufficient information for determining sheet caliper, i.e. the thickness d. For this discussion, the emitted signal 60 is assumed to be a single (infinitely) short pulse. For such a short pulse, caliper can be determined from the following: The difference in arrival time of the double transmitted reflected pulse for the cases with sheet material 2 (FIG. 3b,c) and without sheet material 2 (FIG. 3a) is expressed as:

$$t^*-t=2(nd-d)/c,$$

where n is the index of refraction of the sheet material 2, d the physical thickness, and c the speed of light in vacuum. Further, the difference in arrival times between the front and back reflection of the paper sheet itself (see FIG. 3b) is expressed as:

$$t2-t1=2nd/c.$$

Once these quantities are known, the caliper d can be obtained through $$2d=c(t2-t1)-c(t^*-t).$$

A realistic wave function is different from an infinitely short pulse, and moreover the refractive index n may be frequency dependent. In such a setting, one possible procedure would consist in identifying a recognizable portion of the emitted waveform (e.g. a peak), and identifying these portions in the detected response 70 for each of the reflected signals shown in FIG. 3b, thereby obtaining the times t1, t2, t*. This illustrates the feasibility, i.e. that sufficient information is contained in the detected response 70 together with the emitted waveform (detected response without the sheet material 2).

The inventors have found that a more stable and reliable algorithm is obtained by determining the parameters n and d using a physical model. This algorithm is illustrated in the block diagram of FIG. 4 in more detail. This algorithm is based on a physical (optical) model 81 that links the paper sheet quality parameters 91 to a predicted waveform 94 (predicted form of the response 70 shown in FIGS. 3b, 3c) as output.

This model 81 has the following components: A map 82 linking the paper sheet quality parameters 91 to the index of refraction n and the thickness d. This map 82 may be the identity in the case of caliper=thickness d, and may contain a parametrization of n, Further, the parameters n and d are mapped to the reflection and transmission coefficients (r, t) 93 at the interfaces between the sheet material 2 and the air gaps 42, 44 (see FIGS. 3a-3c), via Fresnel equations 83. Therein, other input parameters may be used (e.g. the index of refraction of air 42, 44).

The model 81 further includes a set of optics equations 84 for calculating a predicted response (predicted detected waveform) 94, using the following input parameters: (i) waveform of the emitted THz radiation signal 72 (i.e. waveform of emitted radiation 60 of FIGS. 3a-3c), and (ii) reflection and transmission coefficients (r, t) 93. Other input parameters may be included as well (e.g. the optical properties of the reflecting material 46, wherein in the case of metal like Au, Cu, Al a 100% reflection can realistically be assumed). These optics equations 84 depend on the detailed geometry but are standard knowledge and obtainable from standard optics textbooks.

The algorithm further includes an error function 85 that expresses a deviation 95 between the predicted response 94 on the one hand and the detected response 74 (waveform of the detected radiation 70 of FIGS. 3b-3c) on the other hand. This error function 85 may, for example, be the $L^2$ norm.

Figure 4:
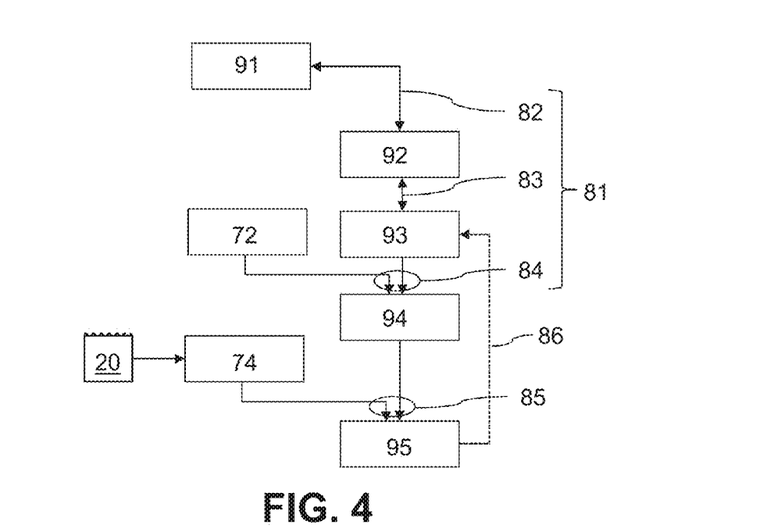
FIG. 4 is a block diagram illustrating a method of determining paper sheet quality parameters according to an embodiment of the invention.

The iterative algorithm uses any one of the parameters 91, 92 or 93 as input parameters (model parameters), since these parameters are linked via the equations 82, 83. In the following the method is described using the transmission and reflection coefficients 93 as input parameters.

In a first step, initial coefficients 93 are set, e.g. random values or plausible initial values. Then, a predicted (simulated) response 94 is calculated based on these initial coefficients 93 using the optics equations 84 as described above. Then, the deviation 95 is calculated using the error function 85. Then the coefficients 93 are varied depending on the coefficients and error function 85 of previous steps. This variation is performed using a strategy that eventually approaches a minimum deviation. For example, a minimization algorithm based on the Levenberg-Marquardt technique can be used.

In this manner, the model parameters 93 are varied and the calculation of the corresponding deviation 94 is repeated (arrow 86), until the deviation 94 satisfies a best-fit criterion (i.e. is sufficiently minimized). Then, the final model parameters 93 are used for calculating the sheet quality parameters 91 (e.g. caliper d) via mappings 83 and 82. In this manner, the sheet quality parameters 91 are determined by calculating a best-fit response 94 that sufficiently minimizes the deviation 95, i.e. such that the predicted response 94 of the physical model fits to the detected response 74.

Since the algorithm takes into account the full waveform of the detected response 74 via the error function 85, and not just individual land-mark features, the result is stable and reliable by the fact that one accounts for each individual frequency component in the appropriate way, given by the physical model.

Figure 5:
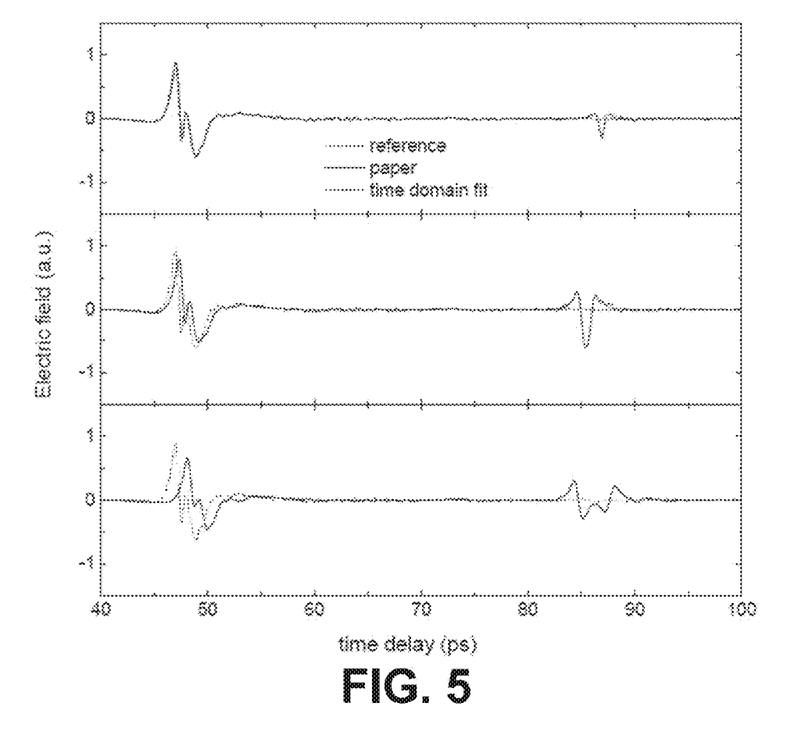
FIG. 5 is a diagram representing the detected and/or simulated time response of the THz radiation having interacted with paper sheet material.

FIG. 5 shows the as-measured time-domain spectra ("paper") of three different kinds of paper sheet material, the corresponding reference spectrum ("reference") corresponding to the setting of FIG. 3a without sheet material, and the best-fit predicted waveform (predicted response 94 of FIG. 4) to the data ("time domain fit") as a function of time. The caliper and basis weight (91 in FIG. 4) are directly obtained from the fitting parameters as described above. The thickness of sheet material from top to bottom is 38 µm, 88 µm and 275 µm.

Next, some aspects for determining base weight w are described. In the case of paper, it has been found that there is a linear relationship between the index of refraction n and mass density, and thus between the optical density n*d and basis weight w:

$$w=a^*n^*d,$$

with a being a proportionality constant. The quantities n (index of refraction) and d (caliper) are obtained from the iterative procedure described with reference to FIG. 4 above. The proportionality constant a can, for example, be obtained from a calibration measurement to many possible varieties of paper that has been performed previously, and is stored in the system memory. The proportionality constant a is valid for all different kinds of paper and board materials, i.e. not dependent on the kind of paper sheet material. Thus, a material-dependent calibration is not needed.

Next, some aspects for determining ash are described. Ash is defined as all minerals that remain when paper is heated up to 525° C. Common examples are calcium carbonate, kaolin, talc and titanium dioxide. These substances absorb THz radiation between 0.01-10 THz giving rise to absorption lines with typical line widths of 0.5-1 THz. The ash content of sheet materials can be obtained from characteristic THz absorption features of the different ashes. These are most easily visible and analyzable in the frequency domain.

The ash content of a sheet material can thus be directly obtained from a spectral weight analysis of the absorption spectrum in the frequency domain. The latter can, for example, be obtained by Fourier transformation of the received response 70 (see FIG. 3c) or a portion thereof or a quantity derived therefrom. According to a particularly advantageous aspect, ash is determined by Fourier analysing a detected time-signal portion including an emitted peak which has traversed the paper sheet material at least twice (e.g. the portion of the response represented by t* in FIGS. 3b and 3c, which corresponds to a double path transmission through the sheet material).

According to an alternative aspect, ash is determined by Fourier analysis of the index of refraction obtained by the iterative method described herein.

Figure 6:
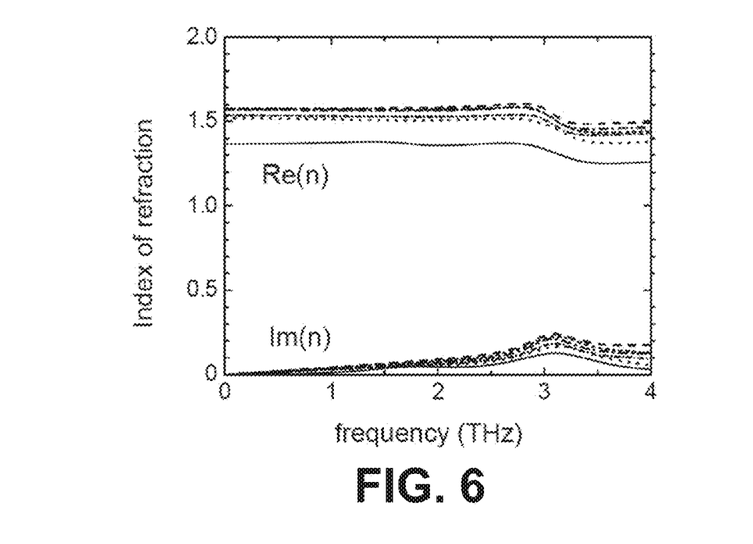
FIG. 6 is a diagram representing the real and imaginary parts of indices of refraction of paper sheet material as determined according to an exemplary embodiment.

FIG. 6 is a diagram representing the real and imaginary parts of indices of refraction of various example paper sheet materials as determined according to an example algorithm of FIG. 4. The paper sheet materials contain calcium carbonate as filler, in various concentrations. Both the real and the imaginary part clearly show an excitation around 3 THz which is due to calcium carbonate.

A spectral weight analysis based on the complex index of refraction is therefore indicative of the ash content of the sheet material. For example, if the index of refraction n is parameterized using eq. (1) above, wherein the function $p_k$ represents the (known) contribution of calcium carbonate to the index of refraction, the ash content may be calculated by analysing the weight $n_k$ of this contribution. Herein, ash content is obtained by multiplying the weight $n_k$ with a conversion factor that is obtained using a (paper-independent) calibration measurement specific for calcium carbonate and that is then stored in the system's memory. Hence, according to an aspect, the ash content is obtained from an analysis of the index of refraction.

Figure 7:
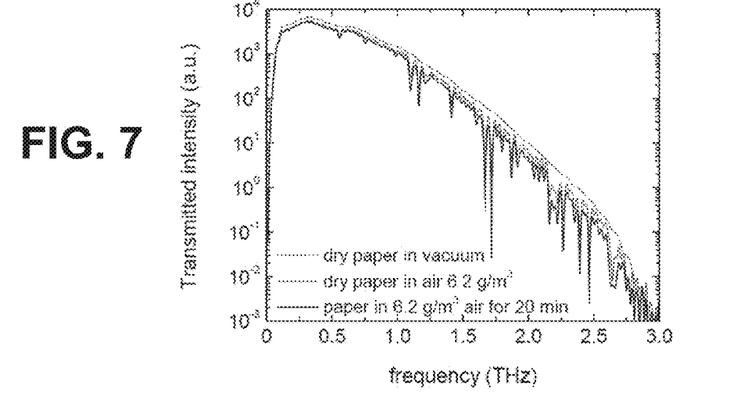
FIG. 7 is a diagram representing the transmission spectra of paper sheet material of various humidities.

Next, some aspects for determining moisture are described. Similarly to ash, also moisture (water) is absorbed at particular frequencies. For illustration, FIG. 7 represents the transmission spectra of paper sheet material of two different humidities ("dry" and "non-dry"). As can be seen from FIG. 7, the absorption spectrum of water in the THz regime is characterized by many sharp and strong absorption lines on top of an absorption background, due to rotational transitions that can be excited with THz photons. FIG. 7 shows the typical spectra of bone dry paper in vacuum, bone dry paper in humid air of 25° C., 29% RH, and moist paper in the same humid air environment. The water absorption lines are clearly visible above 0.5 THz.

The moisture content of a sheet material can be obtained using these characteristic absorption lines in the frequency domain. As a general aspect, the water content (moisture) can be calculated in an analogous manner as ash. Different from ash, the contribution to the index of refraction due to water may be described by an additional term added to eq. (1), the additional term being $w*n_w(f)$. Herein, w is a weight factor of water (model parameter to be determined), and $n_w(f)$ is the refractive index change due to a unit quantity of water moisture (stored in the system memory).

Alternatively, in a configuration of FIG. 2b, the water content (moisture) can be obtained directly by an optical transmission measurement. From the transmitted radiation, a frequency-range absorption spectrum such as the one shown in FIG. 7 is obtained, which allows quantifying the moisture due to the characteristic absorption pattern of water in the THz range. To this purpose, either the full absorption spectrum or one or more individual absorption peaks thereof may be analysed.

A particularity of moisture is that since the THz beam also transverses ambient air which generally also has some humidity content, there is additional absorption per unit length due to this ambient humidity, in addition to the moisture in the sheet 2. This ambient humidity can be taken into account by adding a further term to the index of refraction of the ambient air, the additional term being $w_a*n_w(f)$. Herein, $w_a$ is a material constant proportional to the humidity content of the ambient air. The parameter $w_a$ can be set, for example, in dependence of a humidity value obtained from the external humidity sensor 26 (and a temperature set by the temperature sensor 28) shown in FIG. 1.

Alternatively, the moisture can at first be calculated as a total moisture (sheet moisture plus quantity of water in air) the radiation is subjected to, e.g. by analysing the absorption measurements as mentioned above. Then, the quantity of water in the air is subtracted from the total moisture, for obtaining the sheet moisture. The quantity of water in the air can, for example, be obtained from the air humidity value obtained from the external humidity sensor 26 and from the temperature sensor 28 shown in FIG. 1 and from the length of the THz beam path. Other than the particularities mentioned herein, the description of the determining of ash also applies to the determining of moisture.

Next, some aspects for determining coat weight are described. Coat weight is obtained in an analogous way to determining the basis weight, e.g. by the iterative algorithm described above. In addition, the coating layer having an index of refraction $n_c$ and a thickness $d_c$ is added to the model. The presence of such a coating on the basis sheet alters the front and/or back reflection amplitudes via the Fresnel equations. This alteration influences the time-domain waveform of the kind shown in FIG. 5 in a characteristic manner. Hence, in an example, in addition to the other model parameters the optical density $n_c*d_c$ of a coating layer is also taken into account in the physical model and is optimized for obtaining a best-fit predicted response.

Figure 8:
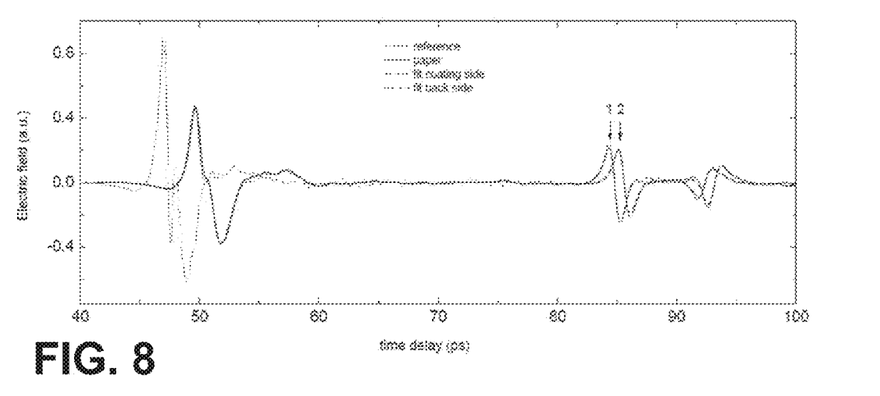
FIG. 8 is a diagram representing the detected time response of the THz radiation having interacted with single coated paper sheet material.

FIG. 8 shows an experimental THz response in the time-domain measured using a setup analogous to the one shown in FIGS. 1, 2a and 3a-3c, wherein the response is obtained using a single sided coated sheet material. Hence, except for this difference in sheet material, the diagram of FIG. 8 is similar to the diagrams of FIG. 5. More precisely, FIG. 8 shows the reference spectrum with no sheet material present in the stack ("reference"), the spectrum of the sheet material with the uncoated side towards the light source (solid line "paper" 1) with best-fit predicted response ("fit coating side") and the sheet material with the coated side towards the light source (solid line "paper" 2) with best-fit predicted response ("fit back side").

In the time-domain response signal shown in FIG. 8, the peak structure around 50 ps time delay is due to a signal component corresponding to the reflection at the reflector material (46) (i.e. the ray marked as t* in FIGS. 3b, 3c). The peak structure around 85 ps time delay (peaks 1 and 2 in FIG. 8) is due to a signal component corresponding to subsequent reflections at the paper-sheet material surface (i.e. the rightmost rays in Fig. c).

As expected, these peaks 1 and 2 are influenced by the presence or absence of coating: FIG. 8 clearly shows differences in the shape of the waveforms reflected from the front and back surface depending on the orientation of the sheet (cf. peak 1 and 2). When the uncoated side is facing the light source (peak 1), the amplitude of the first part of the waveform (which here includes the reflection of the coating) is larger than when the coated side is turned towards the light source (peak 2). The lower amplitude in the latter case is due to the dull appearance of the uncoated side also at THz frequencies. These changes allow for a well determined set of data for obtaining the optical thickness of the coating $n_c*d_c$ as described above (e.g. using the iterative algorithm described above), even in the case only spectrum 1 or 2 is obtained.

The coating weight is proportional to the determined optical thickness and can therefore be obtained from the latter, as described above for the basis weight: Namely, analogously as for the basis weight analysis, a factor of proportionality between the optical density of the coating $n_c*d_c$ and coat weight gives a single value calibration constant independent of the material. By multiplying the determined optical density of the coating with this proportionality factor, the coating weight is obtained.

Finally, some details of the determining of the fiber orientation and fiber anisotropy are described with reference to FIG. 9. Fibrous materials often have a preferred alignment of their constituents which creates linear birefringence. As a result, the index of refraction along and perpendicular to the fiber orientation can be slightly different. The fiber orientation and anisotropy is determined by emitting THz radiation of at least two different polarization states (e.g. linear polarization states) onto the sheet material and analyzing changes of the respective polarization states after interaction with the paper using a polarization-state-sensitive detection system. In the presence of birefringence, the paper induces rotation of the polarization states. The fiber orientation (direction) and anisotropy (magnitude) is obtained by measuring the direction and magnitude of the birefringence axis, i.e., of n.

Figure 9:
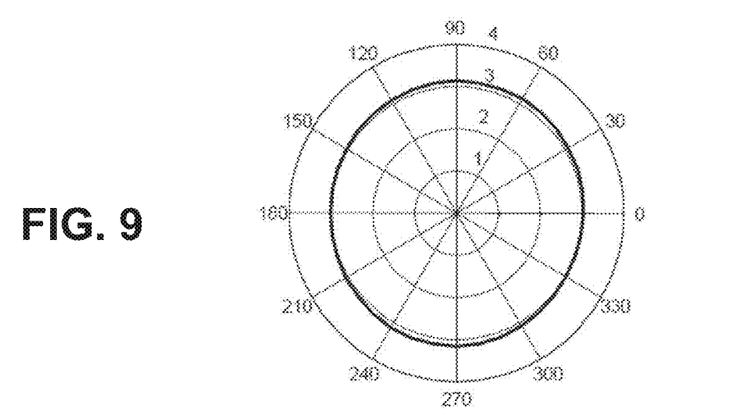
FIG. 9 is a diagram representing the transmission amplitude data of paper sheet material as a function of rotation angle of the paper sheet material.

FIG. 9 is a diagram representing the transmission amplitude of paper sheet material (in a measurement using the setup shown in FIG. 2b) as a function of rotation angle of the polarization direction with respect to the paper sheet material. Namely, linearly polarized THz radiation is shined onto the sheet material and then detected using a detector for detecting the polarization state emitted by the emitter (having an analyzer filter functionality which projects the radiation onto the polarization state emitted by the emitter).

Then the analyzer and detector are rotated relative to the sheet material (e.g. by rotating the sheet material). FIG. 8 shows the amplitude of the transmission of the paper as a function of the rotation angle. In case of zero linear birefringence in the sheet material, the curve in FIG. 8 would be a perfect circle. However, the experimental transmission amplitude can be seen to be slightly elliptical with the major axis of the ellipse oriented at a non-zero value. The angle of the main axis of the ellipse indicates the fiber orientation angle of the sheet material. The ratio of major to minor axis indicates the fiber anisotropy in the sheet material.

The measurement setup can be varied. For example, the emitter may emit circularly polarized radiation or some other radiation having no preferred linear polarization axis; and the detector may be adapted for detecting the polarization state at some (rotatable) angle (e.g. by a rotatable linear polarization filter being arranged as an analyser in front of the detector, and/or by using a polarization-sensitive detector e.g. having detection antennae aligned for detecting radiation of a particular linear polarization). In these cases, the resulting detected intensity as a function of linear polarization angle has the same qualitative features as the result shown in FIG. 9, and is analysed in the manner as described in the following.

For determining the fiber anisotropy, measurements such as the ones shown in FIG. 9 can be analysed as follows: The detected radiation intensity shown in FIG. 9 as a function of angle has a periodicity of $\pi$ (180°).

Generally, and independently of the details of the measurement setup, the detector includes a linear-polarization analyser, and the radiation intensity detected by the detector can be written as $$I(\alpha - \alpha_0).$$

Therein, $I(\phi)$ is a function of periodicity $\pi$ describing the intensity as a function of angle $\alpha$ between the detector axis of the detector's linear-polarization analyser and the main optical axis of the paper sheet material, wherein $\phi=0$ corresponds to parallel alignment between both axes. Here, the angle $\phi$ is a priori unknown, and only the detector angle $\alpha=\phi+\alpha_0$ relative to the laboratory system is known. Here, $\alpha_0$ is the (a priori unknown) offset angle describing the difference between the main optical axis of the paper sheet material and the laboratory angle.

The detailed functional form of $I(\phi)$ depends on the geometry of the measurement setup and on the transmission coefficients of the paper sheet material, and can be analytically obtained using standard optics equations (see, e.g., H. G. Tompkins, Handbook of ellipsometry, 2005). Generally, and independently of the detailed measurement setup, the function $I(\phi)$ has extrema (minimum and maximum, respectively) at $\phi=0$ and at $\phi=\pi/2$, and their difference $|I(0)-I(\pi/2)|$ depends on the optical anisotropy.

Finding the optical axis of the paper sheet material amounts thus to finding the offset angle $\alpha_0$. Since the detailed functional form of $I(\phi)$ is known (except for the value of the transmission coefficients of the paper sheet material), the fiber orientation can be obtained numerically from plural measurements $I_i$ at different angle $\alpha_i$, (e.g. two or three measurements) by resolving the resulting equations $I_i=I(\alpha_i)$ for the unknown parameters $\alpha_0$ and the transmission coefficients, from the (known) functional form of $I(\phi)$.

Preferably, two or three measurements ($I_1$, $I_2$ and optionally $I_3$) are obtained. Then, the results are resolved for the three unknown quantities (offset angle $\alpha_0$ as well as the transmission coefficients for both polarization axes). Two measurements are sufficient if the geometry setup/the relative angle of both measurements is chosen such that both measurements depend only on a particular combination of the two transmission coefficients. In general, this is possible if the angle between the different polarization directions of the detector is different from 90°.

Hence, according to a general aspect, the response for at least two (linear) polarization directions is detected distinctly; and the optical axis (offset angle $\alpha_0$), i.e. one of the optical axes, is determined from respective intensities of the detected responses, in particular from fitting the offset angle $\alpha_0$ to a function $I(\alpha-\alpha_0)$ wherein $I(\phi)$ is a periodic function having an extremum at 0.

According to a general aspect, the THz detector is configured for detecting at least two (linear) polarization directions is detected distinctly, wherein preferably the angle between two of the polarization directions of the detector is different from 90°.

Then, the responses may be linearly combined such as to transform them into an axis-frame (i.e. components parallel and perpendicular to the determined optical axis). In case of the (linear) polarization being orthogonal, this is a rotation by the offset angle $\alpha_0$. Otherwise, it is a more general linear transformation mapping the detection-frame responses to the axis-frame.

Alternatively, model parameters can be calculated from the response in the detection-frame, and the model parameters are then transformed (rotated or linearly combined) to the axis-frame.

In terms of the graph shown in FIG. 9, the procedure can be described by measuring the intensity in a few directions (i.e. collecting a few of the measurements shown in FIG. 9, for example at 0° and 60°); and obtaining the optical axis by determining an angle offset from these measured intensities. Then, either the measured optical response itself or model parameters derived from the optical response are transformed to the axis-frame.

In addition, not only the offset angle $\alpha_0$, but also the anisotropy can be calculated from the measured intensities. The anisotropy can be obtained by resolving the equations $I_i = I(\alpha_i)$ as described above. Alternatively, the model parameters are obtained in the axis-frame as described above, and then the anisotropy a is calculated in the axis-frame as $$a = (2\pi/\lambda) \times d \times Re(n_1 - n_2),$$

Herein, $\lambda$ is the wavelength of the radiation, d is the thickness of the paper sheet material, and $n_1$ and $n_2$ are the refraction coefficients measured along the optical axes. Thus, once the (real parts of) the indices of refraction along the respective optical axes of the paper sheet material are obtained, the (frequency-dependent) anisotropy can be obtained using the above formula.

FIG. 9 shows a quasi-continuous number of transmission measurements as a function of angle, which allows the main axes of the measured ellipse (fiber orientation) to be extracted.

Generally, as described above, the optical axes and their aspect ratio can be obtained from three such transmission measurements at three different angles. Hence, according to a general aspect, the detector is sensitive to at least three different polarizations. This is achievable by providing a detector system having individual detector outputs for each of the linear polarizations. The detector system may comprise separate detectors, one for each of the linear polarizations, or may comprise a detector having individual antenna patterns, one for each of the linear polarizations. The antenna patterns may overlap or be provided in separate detection regions of the detector. The emitted radiation may be a radiation of known polarization, e.g. a circularly polarized emitted radiation or radiation having the same polarization(s) as the detected radiation.

Once the optical axis is obtained, it is advantageous to calculate the remaining parameters in an axis-frame. To this purpose, the polarization components of the detected response signal are linearly combined (rotated) to an axis-frame, with one component parallel to the fiber direction (main optical axis) and one component orthogonal to the fiber direction.

According to a preferable general aspect, the fiber orientation is determined first; then the detected response is transformed to the axis frame, and then the remaining quality parameters are determined using the axis-frame response.

While the foregoing is directed to embodiments, other and further embodiments may be devised without departing from the basic scope determined by the claims.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. Method of determining a plurality of paper sheet quality parameters of a paper sheet material based on fitting to a physical model by a non-contact sensor system, wherein the paper sheet quality parameters include at least sheet caliper, basis weight, and sheet moisture, and wherein the sensor system includes an emitter system for emitting THz radiation, a detector system for detecting THz radiation, and a processing unit operationally coupled to the emitter system and the detector system, the method comprising:

emitting, by the emitter system, a THz radiation signal towards the paper sheet material such that the THz radiation interacts with the paper sheet material;

detecting, by the detector system, a time and/or frequency dependent response of the THz radiation signal having interacted with the paper sheet material;

determining model parameters of the physical model by optimizing the model parameters such that a simulated response of the physical model is fitted to the detected response, the model parameters being indicative of transmission and/or reflection coefficients at interfaces of the paper sheet material with surrounding media; and determining, from the determined model parameters, at least one of the paper sheet quality parameters, whereby the model parameters of the physical model are fitted to the detected response by an iterative procedure comprising:

(a) calculating a simulated response based on the physical model using an initial guess for the model parameters;

(b) calculating an error function expressing a deviation between the simulated response and the detected response;

(c) iterating steps (a) and (b), whereby the model parameters are varied until the error function satisfies a best-fit criterion; and (d) obtaining fitted model parameters as final parameters satisfying the best-fit criterion in step (c), and calculating at least one of the paper sheet quality parameters from the fitted model parameters.

2. The method according to claim 1, wherein the paper sheet quality parameters include fiber orientation and optionally fiber anisotropy of the paper sheet material, and wherein the detector system is sensitive to polarized THz radiation of mutually different polarization states, the method comprising:

emitting the THz radiation signal by the emitter system with more than one linearly polarized component;

detecting the detected time and/or frequency dependent response for each of the two polarization directions;

determining the model parameters as respective set of detection-frame model parameters for each of the two polarization directions, the detection-frame model parameters being indicative of the transmission and/or reflection coefficients at the interfaces of the paper sheet material with the surrounding media in the respective polarization direction;

determining, from the detection-frame model parameters, the fiber orientation as an optical axis of the paper sheet material;

combining the detection-frame model parameters dependent on an angle between the respective polarization directions and the determined optical axis, thereby obtaining axis-frame model parameters indicative of the transmission and/or reflection coefficients at the interfaces of the paper sheet material with the surrounding media for a direction parallel to the determined optical axis and for a direction perpendicular to the determined optical axis, respectively; and determining at least one of the remaining paper sheet quality parameters from the axis-frame parameters.

3. The method according to claim 2, wherein at least one of the fiber orientation and the fiber anisotropy is determined dependent on frequency.

4. The method according to claim 1, comprising:
determining the model parameters using a detected response covering a time of at least 500 fs and having a time resolution of at least 100 fs.

5. The method according to claim 1, wherein all of the paper sheet quality parameters are determined from a single THz radiation signal.

6. The method according to claim 1, wherein the sensor system includes a back-side THz reflector, and wherein the emitter system and the detector system are arranged on one side of the paper sheet material and the back-side THz reflector is arranged on the other side of the paper sheet material.

7. The method according to claim 1, wherein the paper sheet quality parameters are determined without input in the physical model of any calibration data specific for a kind of paper sheet material.

8. The method according to claim 1, wherein the sensor system includes an air moisture sensor and a temperature sensor operationally coupled to the processing unit, the method comprising:
obtaining an ambient air moisture value from the air moisture sensor, obtaining a temperature value from the temperature sensor, and inputting the obtained temperature value and the ambient air moisture value to the processing unit.

9. The method according to claim 1, comprising:
inputting a reference signal sequence in the physical model, wherein the reference signal sequence describes the emitted THz radiation signal not having interacted with the paper sheet material.

10. The method according to claim 1, wherein the determined model parameters include a parametrization of the index of refraction, wherein ash and moisture are determined by spectral analysis of the determined index of refraction.

11. The method according to claim 1, comprising:
moving the emitter system and the detector system transversally with respect to a feeding direction of the paper sheet material.

12. Sensor system for determining a plurality of paper sheet quality parameters of a paper sheet material in a non-contact manner, the sensor system comprising:
an emitter system for emitting THz radiation;
a detector system for detecting THz radiation; and
a processing unit operationally coupled to the emitter system and the detector system, and configured for determining the plurality of paper sheet quality parameters by:
emitting, by the emitter system, a THz radiation signal towards the paper sheet material such that the THz radiation interacts with the paper sheet material;
detecting, by the detector system, a time and/or frequency dependent response of the THz radiation signal having interacted with the paper sheet material;
determining model parameters of the physical model by optimizing the model parameters such that a simulated response of the physical model is fitted to the detected response, the model parameters being indicative of transmission and/or reflection coefficients at interfaces of the paper sheet material with surrounding media; and
determining, from the determined model parameters, at least one of the paper sheet quality parameters, whereby the model parameters of the physical model will be fitted to the detected response by an iterative procedure comprising:
(a) calculating a simulated response based on the physical model using an initial guess for the model parameters;
(b) calculating an error function expressing a deviation between the simulated response and the detected response;
(c) iterating steps (a) and (b), whereby the model parameters are varied until the error function satisfies a best-fit criterion; and
(d) obtaining fitted model parameters as final parameters satisfying the best-fit criterion in step (c), and calculating at least one of the paper sheet quality parameters from the fitted model parameters.

13. Apparatus according to claim 12, for handling paper sheet material, the apparatus comprising:
a paper sheet feeding system for feeding the paper sheet material, the sensor system being arranged for determining a plurality of paper sheet quality parameters while the paper sheet material is being transported by the paper sheet transport system.

14. Apparatus for handling paper sheet material according to claim 13, the apparatus comprising:
at least one paper processing section, and a control section, the control section being configured to adjust operation of the at least one paper processing section dependent on the paper sheet quality parameters determined by the sensor system.

15. Method according to claim 1, wherein the at least one paper sheet quality parameter includes the fiber anisotropy.

16. The method according to claim 3, comprising:
determining the model parameters using a detected response covering a time of at least 500 fs and having a time resolution of at least 100 fs.

17. The method according to claim 16, wherein all of the paper sheet quality parameters are determined from a single THz radiation signal.

18. The method according to claim 8, wherein the determined model parameters include a parametrization of the index of refraction, wherein ash and moisture are determined by spectral analysis of the determined index of refraction.

19. The apparatus according to claim 12, wherein the sensor system includes a back-side THz reflector, and wherein the emitter system and the detector system are arranged on one side of the paper sheet material and the back-side THz reflector is arranged on the other side of the paper sheet material.

20. The apparatus according to claim 19, wherein the sensor system comprises:
an air moisture sensor and a temperature sensor operationally coupled to the processing unit, the processing unit being configured for obtaining an ambient air moisture value from the air moisture sensor, and obtaining a temperature value from the temperature sensor for input to the processing unit.

* * * * *